US009668967B2

(12) United States Patent
Nistor et al.

(10) Patent No.: US 9,668,967 B2
(45) Date of Patent: Jun. 6, 2017

(54) LIPID FORMULATIONS COMPRISING A THIOLATED ANTIOXIDANT

(75) Inventors: Catalin Nistor, Lund (SE); Fredrik Tiberg, Lund (SE); Krister Thuresson, Lund (SE); Markus Johnsson, Lund (SE)

(73) Assignee: CAMURUS AB (SE)

( * ) Notice: Subject to any disclaimer, the term of this patent is extended or adjusted under 35 U.S.C. 154(b) by 822 days.

(21) Appl. No.: 13/060,121

(22) PCT Filed: Aug. 21, 2009

(86) PCT No.: PCT/GB2009/002054
§ 371 (c)(1),
(2), (4) Date: May 12, 2011

(87) PCT Pub. No.: WO2010/020794
PCT Pub. Date: Feb. 25, 2010

(65) Prior Publication Data
US 2011/0230569 A1    Sep. 22, 2011

(30) Foreign Application Priority Data
Aug. 22, 2008 (GB) .................................. 0815435.3

(51) Int. Cl.
| A61K 47/10 | (2006.01) |
| A61K 9/00  | (2006.01) |
| A61K 9/127 | (2006.01) |
| A61K 47/14 | (2017.01) |
| A61K 47/24 | (2006.01) |

(52) U.S. Cl.
CPC .......... *A61K 9/0024* (2013.01); *A61K 9/1274* (2013.01); *A61K 47/10* (2013.01); *A61K 47/14* (2013.01); *A61K 47/24* (2013.01)

(58) Field of Classification Search
USPC ....................................................... 514/777
See application file for complete search history.

(56) References Cited

U.S. PATENT DOCUMENTS

| 4,938,763 | A   |   | 7/1990  | Dunn et al. |  |
|-----------|-----|---|---------|-------------|--|
| 5,340,802 | A   |   | 8/1994  | Shiosaki et al. | |
| 5,480,656 | A   |   | 1/1996  | Okada et al. | |
| 5,531,925 | A   |   | 7/1996  | Landh et al. | |
| 5,639,480 | A   |   | 6/1997  | Bodmer et al. | |
| 5,776,885 | A   |   | 7/1998  | Orsolini et al. | |
| 5,807,573 | A   |   | 9/1998  | Ljusberg-Wahren et al. | |
| 5,955,502 | A   | * | 9/1999  | Hansen et al. | 514/558 |
| 6,011,067 | A   | * | 1/2000  | Hersh | 514/562 |
| 6,066,328 | A   |   | 5/2000  | Ribier et al. | |
| 6,113,943 | A   |   | 9/2000  | Okada et al. | |
| 6,228,383 | B1  |   | 5/2001  | Hansen et al. | |
| 6,458,924 | B2  |   | 10/2002 | Knudsen et al. | |
| 6,464,987 | B1  |   | 10/2002 | Fanara et al. | |
| 8,097,239 | B2  | * | 1/2012  | Johnsson et al. | 424/9.2 |
| 8,182,834 | B2  |   | 5/2012  | Johnsson et al. | |
| 8,187,629 | B2  |   | 5/2012  | Barauskas et al. | |
| 8,236,292 | B2  |   | 8/2012  | Thuresson et al. | |
| 8,236,755 | B2  |   | 8/2012  | Thuresson et al. | |
| 2002/0026027 | A1 |   | 2/2002  | Ansell | |
| 2003/0022242 | A1 |   | 1/2003  | Anderson | |
| 2004/0018241 | A1 |   | 1/2004  | Houze et al. | |
| 2004/0201117 | A1 |   | 10/2004 | Anderson | |
| 2005/0136059 | A1 |   | 6/2005  | Thorpe et al. | |
| 2006/0046301 | A1 | * | 3/2006  | Happe | 436/71 |
| 2006/0073203 | A1 |   | 4/2006  | Ljusberg-Wahren et al. | |
| 2007/0080323 | A1 |   | 4/2007  | Joabsson et al. | |
| 2007/0110777 | A1 |   | 5/2007  | Joabsson et al. | |
| 2007/0134336 | A1 |   | 6/2007  | Worle et al. | |
| 2007/0231374 | A1 |   | 10/2007 | Tiberg et al. | |
| 2008/0124394 | A1 |   | 5/2008  | Johnsson et al. | |
| 2008/0146490 | A1 |   | 6/2008  | Joabsson et al. | |
| 2008/0161276 | A1 |   | 7/2008  | Johnsson et al. | |
| 2008/0214995 | A1 |   | 9/2008  | Boyd et al. | |
| 2008/0274176 | A1 |   | 11/2008 | Johnsson et al. | |
| 2009/0069221 | A1 |   | 3/2009  | Joabsson et al. | |
| 2009/0155193 | A1 |   | 6/2009  | Joabsson et al. | |
| 2009/0170782 | A1 |   | 7/2009  | Joabsson et al. | |
| 2010/0210519 | A1 |   | 8/2010  | Johnsson et al. | |
| 2012/0028890 | A1 |   | 2/2012  | Nistor et al. | |
| 2012/0269772 | A1 |   | 10/2012 | Thuresson et al. | |

FOREIGN PATENT DOCUMENTS

| EP | 1600162 | 11/2005 |
| WO | WO 93/06921 A1 | 4/1993 |
| WO | WO 95/34287 A1 | 12/1995 |
| WO | WO 97/13528 A1 | 4/1997 |
| WO | WO 98/47487 A1 | 10/1998 |
| WO | WO 02/02716 A2 | 1/2002 |

(Continued)

OTHER PUBLICATIONS

International Search Report of PCT International Application Application PCT/GB2009/002054 dated Nov. 30, 2009.
Written Opinion of PCT International Application Application PCT/GB2009/002054 dated Nov. 30, 2009.
About Sandostatin: Proven Control of GH, 1GF-1 and Gastrointestinal Hormone, from www.sandostatin.com/about.sandostatin/index.html and linked documents.
"Acromegaly" from www.niddk.nil.gov/health/endo/pubs/acro/acro.htm.
American Peptide Company, Product Details "Somatostatin and analogs," from www.americanpeptide.com/.
N. Ardjomand et al., "Expression of Somatostatin Receptors in uveal melanomas," Inv. Opthalmol. & Vis. Sci., 2003, vol. 44, No. 3, pp. 980-987.
Barauskas et al., Pharmaceutical Nanotechnology, "Interactions of lipid-based liquid crystalline nanoparticles with model and cell membranes," International Journal of Pharmaceutics 391 (2010) pp. 284-291.
R. Berges, "Eligard: Pharmacokinetics, Effect on Testosterone and PSA Levels and Tolerability," European Urology Supplements, 2005, vol. 4, pp. 20-25.

(Continued)

*Primary Examiner* — Svetlana M Ivanova
(74) *Attorney, Agent, or Firm* — J.A. Lindeman & Co., PLLC

(57) ABSTRACT

The present invention provides a formulation comprising:
i) a lipid matrix;
ii) at least one thiolated antioxidant;
iii) optionally at least one bioactive agent; and
iv) optionally at least one chelating agent.

13 Claims, 3 Drawing Sheets

(56) References Cited

FOREIGN PATENT DOCUMENTS

| WO | WO 02/066014 A2 | 8/2002 |
|---|---|---|
| WO | WO 02/068561 A2 | 9/2002 |
| WO | WO 02/068562 A2 | 9/2002 |
| WO | WO 03/002136 A2 | 1/2003 |
| WO | WO 03/057235 A2 | 7/2003 |
| WO | WO 2004/087215 A1 | 10/2004 |
| WO | WO 2005/014162 A1 | 2/2005 |
| WO | WO 2005/021022 A2 | 3/2005 |
| WO | WO 2005/046642 A1 | 5/2005 |
| WO | WO 2005/048952 A2 | 6/2005 |
| WO | 2005/063213 A1 | 7/2005 |
| WO | WO 2005/070394 A2 | 8/2005 |
| WO | 2005/117830 A1 | 12/2005 |
| WO | WO 2005117830 A1 * | 12/2005 |
| WO | WO 2006/075123 A1 | 7/2006 |
| WO | WO 2006/075124 A1 | 7/2006 |
| WO | WO 2006/075125 A1 | 7/2006 |
| WO | WO 2006/077362 A1 | 7/2006 |
| WO | WO 2006/131730 A1 | 12/2006 |
| WO | WO 2008/152401 A1 | 12/2008 |
| WO | 2009/024795 A1 | 2/2009 |
| WO | 2009/024797 A1 | 2/2009 |
| WO | WO 2009/024795 A1 | 2/2009 |
| WO | WO 2010/020794 A1 | 2/2010 |

OTHER PUBLICATIONS

Chang, J., "Use of GnRH agonists in the treatment of hyperandrogenism and hirsutism," print out from http://patients.uptodate.com.

P. Chanson et al., "Comparison of octreotide acetate LAR and lanreptide SR in patients with acromegaly," Clin. Endocrinology, 2001, vol. 54, No. 1, pp. 11-13, (Abstract only).

Comets et al., "Non parametric analysis of the absorption profile of octreotide in rabbits from long-acting release formulation OncoLAR," J. Controlled Release 59:197-205 (1999).

F. Dall'Antonia, "Structure determination of organo-silicon compounds.", pp. 6 to 8 from http://shelx.uni-ac.gwdg.de/-fabio/endwkcon.htm.

Definition of analog from http://cancerweb.ncl.ac.uk!omd/about.html, pp. 1-5. Accessed Jul. 7, 2005.

B. L. Erstad, "Octreotide for acute variceal bleeding," Ann. Pharmacother., 2001, vol. 35, No. 5, pp. 618-626. (Abstract only).

FDA's 510(k) Summary of Camurus AB, episil® K101769.

A. K. Flogstad et al., "Sandostatin LAR in acromegalic patients: long term treatment," J. Clinical Endocrinology & Metabolism, 1997, vol. 82, No. 1, pp. 23-28.

P. R. Gibson & J. G. Muir, "Reinforcing the mucus: a new therapeutic approach for ulcerative colitis," Gut, 2005, vol. 54, pp. 900-903.

L. M. Grant & F. Tibert, "Normal and Lateral Forces between Lipid Covered Solids in Solution: Correlation with Layer Packing and Structure," Biophysical Journal, 2002, vol. 82, pp. 1373-1385.

B.A. Hills, "Surface-active phospholipid: a Pandora's box of clinical applications. Part II. Barrier and lubricating properties," Internal Medicine Journal, 2002, vol. 32, pp. 242-251.

G. G. Holz et al., "Glucagon-Like Peptide-1 Synthetic Analogs: New Therapeutic Agents for Use in the Treatment of Diabetes Mellitus," Current Medicinal Chemistry (2003), vol. 10, pp. 2471-2483.

H. Hui et al., "Structure and function studies of glucagon-like peptide-1 (GLP-1): the designing of a novel pharmacological agent for the treatment of diabetes," Diabetes Metabolism Research and Reviews, (2005), vol. 21, pp. 313-331.

Indications and Usage of Eligard, pp. 1-5, print out from http:ffw-ww.rxlist.com.

Information About Buprenorphine Therapy, print out from http://buprenorphine.samhsa.gov/about.html, pp. 1-4.

Information on Goserelin Acetate print out form http://www.bachem.com/.

Information on Goserelin Subcutaneous, Monograph—Goserelin Acetate, pp. 1-7, print out form www.medscape.com.

Information on Leuprolide Intramuscular, Monograph—Leuprolide Acetate, pp. 1-20, print out for www.medscape.com.

Information on Leuprolide (3 Month) Intramuscular, Monograph—Leuprolide Acetate, pp. 1-20, print out from www.medscape.com.

Invitrogen, "Pluronic F-127," Molecular Probes Invitrogen Detection Technologies, pp. 1-2, 2008.

Johnsson et al., "Physicochemical and Drug Delivery Aspects of Lipid-Based Liquid Crystalline Nanoparticles: A Case Study of Intravenously Administered Propofol," Journal of Nanoscience and Nanotechnology, vol. 6, No. 9/10, pp. 3017-3024, 2006.

Kamo, et al., "Nonlamellar Liquid Crystalline Phases and Their Particle Formation in the Egg Yolk Phosphatidylcholine/Diolein System," Langmuir, vol. 19, pp. 9191-9195, Published on Web Oct. 1, 2003.

Kesisoglou, et al., "Liposomal Formulations of Inflammatory Bowel Disease Drugs: Local versus Systemic Drug Delivery in a Rat Model," Pharmaceutical Research, vol. 22, No. 8, Aug. 2005, pp. 1320-1329.

J. G. M. Klijn et al., "Combined tamoxifen and luteinizing hormone-releasing hormone (LHRH) agonist versus LHRH agonist alone in premenopausal advanced breast cancer: A meta-analysis of four randomized trials," Journal of Clinical Oncology, 2001, vol. 19, No. 2, pp. 343-353 (Abstract only).

L. M. Knudsen, "Glucagon-like Peptide-1: The Basis of a New Class of Treatment for Type 2 Diabetes," J. Med. Chem. (2004), vol. 47, pp. 4128-4134.

L. M. Knudsen et al., "Potent Derivatives of Glucagon-like Peptide-1 with Pharmacokinetic Properties Suitable for Once Daily Administration," J. Med. Chem. (2000) vol. 43, pp. 1664-1669.

I. Lancranjan et al., "Sandostatin LAR: Pharmacokinetics. Pharmacodynamics, Efficacy and Tolerability in Acromegalic Patients," Metabolism, 1995, vol. 44, No. 1, pp. 18-26.

"Leutinizing Hormone Releasing Hormone (LHRH) Agonists: Goserelin (Zoladex) vs. Leuprolide (Lupron) for Prostate Cancer," DoD Pharmacoeconomic Center Update, Newsletter, Dec. 2000, vol. 1, No. 1, print out from http://www.pec.ha.osd.mil.com, pp. 1-3.

Loughrey et al., "Development of a Sensitive Sandwich ELISA for Detecting Full Length Biologically Active TH0318, a GLP-1 Analogue," presented at the 2005 AAPS Annual Meeting and Exposition, Abstract No. W5009.

Martel et al., "Enzyme Linked Immunosorbent Assay (EUSA) Method for the Determination of TH0318, a New GLP-1 Analogue in Development for Diabetes," presented at the 2005 MPS Annual Meeting and Exposition, Abstract No. W5008.

Martel et al., "Enzyme Linked !mmunosorbent Assay (EUSA) Method for the Determination of TH0318, a New GLP-1 Analogue in Development for Diabetes," Poster.

MSDS for Ethylene Glycol and Abbreviations used in Toxicity data.

Novartis Pharmaceuticals Corporation, "Sansdostatin LAR Depot (octreotide acetate for injectable suspension)", pp. 1-19.

PDR Information on Eligard 30 mg (Sanofi-Synthelabo), print out from www.Drugs.com, pp. 1-14.

Pharmaceutical Information on LUPRON DEPOT, print out from www.rxmed.com, pp. 1-8.

Product Information on Zoladex Goserelin Acetate Implant (Equivalent to 10.8 mg goserelin).

Product Specification of Leuprolide by GL Biochem, print out from http://www.glschina.com.

Published Data Provided by Sandostatin LAR "The Latest Research and Treatment Information for Pituitary Disorders" from http://www.sandostatin.com/published data/index.html.

O. Sartor "Eligard: Leuprolide Acetate in a Novel Sustained-Release Delivery System," Urology, 2003, vol. 61, (Supplement 2A), pp. 25-31.

K. J. Schuh et al., "Onset, magnitude and duration of opioid blockade produced by buprenorphine and naltrexone in humans," Psychopharmacology, (Berl), Jul. 1999, vol. 145, No. 2, pp. 162-174 (Abstract only).

(56) References Cited

OTHER PUBLICATIONS

J. C. Shah et al., "Cubic phase gels as drug delivery systems," Advanced Drug Delivery Reviews, 2001, vol. 47, pp. 229-250.
"Setting new standards of care," Mixing and Administration instructions for Sandostatin LAR.
W. Stremmel et al., "Retarded release phosphatidylcholine benefits patients with chronic active ulcerative colitis," Gut, 2005, vol. 54, pp. 966-971.
A Sturm & A. U. Dignass, "Modulation of gastrointestinal wound repair and inflammation by phospholipids," Biochimica et Biophysica Acta, 2002, vol. 1582, pp. 282-288.
Svanberg et al., "A New Preventive Strategy Using a Bioadhesive Oromucosal Lipid Solution and Oral Cryotherapy to Protect the Oral Cavity—And Reduce the Need for Total Parenteral Nutrition (Tpn) for Patients Undergoing Autologous Stemcell Transplantation," Support Care Cancer 18 (Suppl 3):S114-S115, at Abstract 08-076 (2010) (attached hereto as Annex 5 to Evidentiary Declaration Under 37 C.F.R. § 1.132 of Fredrik Tiberg).
Tiberg et al., "Drug delivery applications of non-lamellar liquid crystalline phases and nanoparticles", J. Drug Del Sci. Tech., 21(1) pp. 101-109, 2011.
Tiberg et al., "Treatment of oral mucositis pain by a bioadhesive barrier forming lipid solution," Camurus (attached hereto as Annex 3 to Evidentiary Declaration Under 37 C.F.R. § 1.132 of Fredrik Tiberg).
Tiberg et al., "Treatment of Oral Mucositis Pain by a Bioadhesive Barrier Forming Lipid Solution," Support Care Center 17(7):918 (2009) (attached hereto as Annex 4 to Evidentiary Declaration Under 37 C.F.R. § 1.132 of Fredrik Tiberg).
Treating Acromegaly, from http://www.sandostatin.com/lreating acromegaly/index.html and linked documents.
Welin et al., "High-dose treatment with a long-acting somatostatin analogue in patients with advanced midgut carcinoid tumours," 2004, Society of the European Journal of Endocrinology, vol. 151, pp. 107-112.
Wermuth, Pure and Appl. Chem, 1998, 70, 1129-1143.
E. Woltering et al., "Octreotide acetate (LAR) dose effect on plasma octreotide levels: Impact on neuroendocrine tumor Management," F. Clin Oncology, 2005 ASCO Annual Meeting Proceedings, vol. 23, No. 16S, pp. 3177 (Abstract only).
E. A. Woltering, "A discussion on the utility of various routes of administration of octreotide acetate," from http://www.carcinoid.org/medpro/docs/WoltPump2005.htm.
International Search Report of PCT/GB2005/004745 dated May 8, 2006.
International Preliminary Report on Patentability of PCT/GB2005/004745 dated Jul. 20, 2007.
Written Opinion of PCT/GB2005/004745 dated May 8, 2006.
International Search Report of PCT/GB2005/04748 dated Mar. 23, 2006.
International Preliminary Report on Patentability of PCT/GB2005/04748 dated Mar. 12, 2007.
Written Opinion of PCT/GB2005/04748 dated Mar. 23, 2006.
International Search Report of PCT/GB2005/04752 dated Mar. 17, 2006.
International Preliminary Report on Patentability of PCT/GB2005/04752 dated Mar. 12, 2007.
Written Opinion of PCT/GB2005/04752 dated Mar. 17, 2006.
International Search Report of PCT/GB2005/004746 dated Mar. 16, 2006.
International Preliminary Report on Patentability and Written Opinion of PCT/GB2005/004746 dated Jul. 17, 2007.
International Search Report of PCT/GB2006/002079 dated Aug. 25, 2006.
International Preliminary Report on Patentability and Written Opinion of PCT/GB2006/002079 dated Dec. 6, 2007.
International Search Report of PCT/GB2008/002035 dated Oct. 6, 2008.
International Preliminary Report on Patentability of PCT/GB2008/002035 Dec. 17, 2009.
Written Opinion of PCT/GB2008/002035 dated Oct. 6, 2008.
International Search Report of PCT/GB2008/002857 dated Jan. 28, 2009.
International Preliminary Report on Patentability and Written Opinion of PCT/GB2008/002857 dated Feb. 24, 2010.
Office Action in U.S. Appl. No. 11/795,243 dated May 12, 2011.
Office Action in U.S. Appl. No. 11/795,243 dated Mar. 22, 2012.
Office Action in U.S. Appl. No. 11/795,249 dated Jul. 19, 2011.
Office Action in U.S. Appl. No. 11/795,249 dated Oct. 25, 2010.
Office Action in U.S. Appl. No. 11/795,250 dated Dec. 21, 2012.
Office Action in U.S. Appl. No. 11/795,250 dated Mar. 18, 2011.
Office Action in U.S. Appl. No. 11/795,250 dated Jun. 24, 2010.
Office Action in U.S. Appl. No. 11/795,242 dated Jan. 10, 2013.
Office Action in U.S. Appl. No. 11/795,242 dated Dec. 23, 2011.
Office Action in U.S. Appl. No. 11/908,740 dated Feb. 14, 2012.
Office Action in U.S. Appl. No. 11/877,935 dated Dec. 21, 2010.
Apr. 23, 2014, Office Action in U.S. Appl. No. 11/795,243.

* cited by examiner

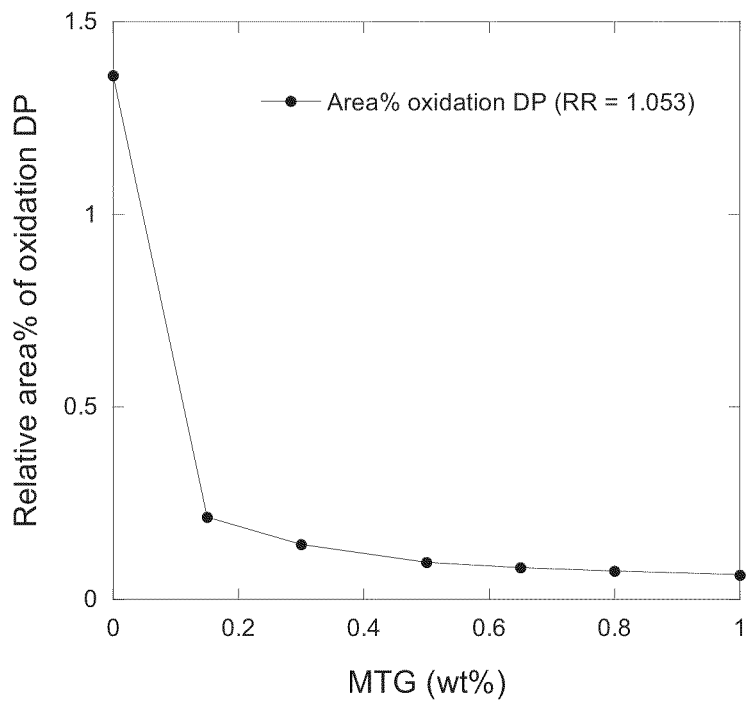
*Figure 1.* Effect of MTG concentration on the protection of BUP in the lipid formulation towards oxidation degradation during stress test with hydrogen peroxide ($H_2O_2$).
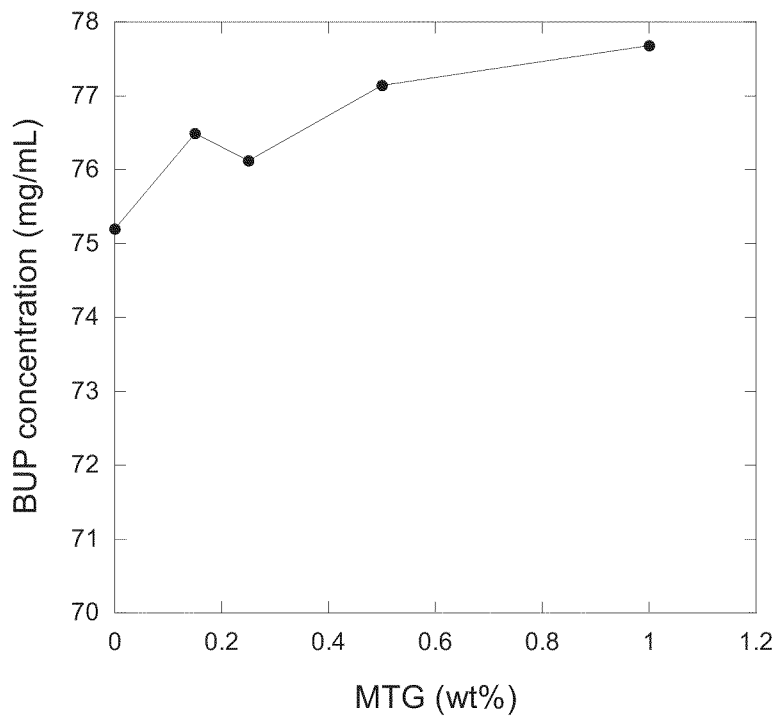
*Figure 2.* Recovery of BUP (free base) after 1 month at 70°C as a function of MTG concentration.

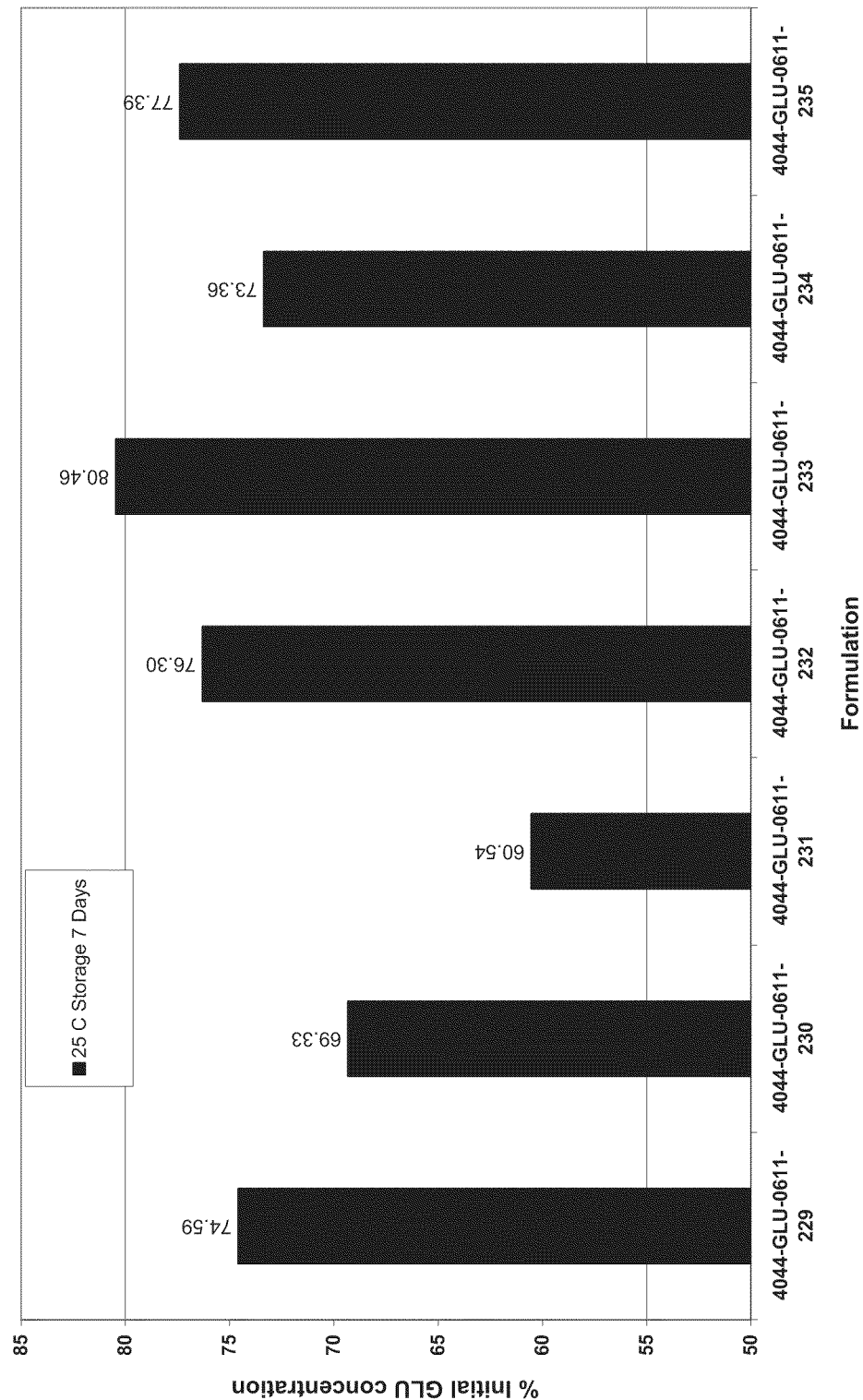
Figure 3. Glucagon concentration (% of the initial value) after storage of the formulations for 7 days at 25°C/60%RH.

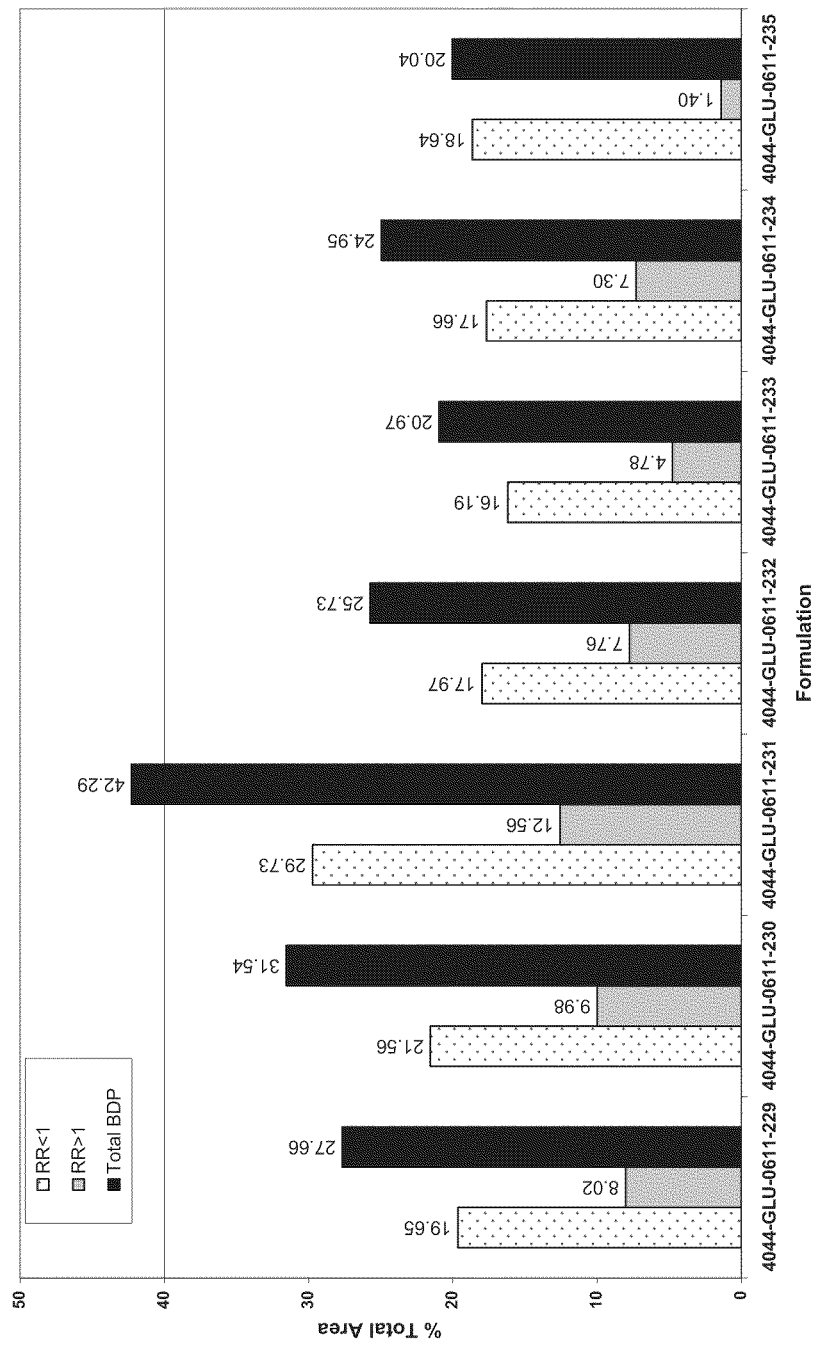
*Figure 4.* The amount of breakdown products (BDP) more hydrophobic (RR < 1) and more hydrophilic (RR > 1) than glucagon, as well as of total amount of BDP (Total BDP) in each formulation tested after storage for 7 days at 25°C/60%RH. Detection wavelength: 214 nm.

LIPID FORMULATIONS COMPRISING A THIOLATED ANTIOXIDANT

FIELD OF THE INVENTION

The present invention relates to lipid formulations and particularly to lipid formulations suitable for administration to subjects. More particularly, the present invention relates to lipid compositions which form non-lamellar phases and in which oxidative degradation is a significant factor with regard to stability. Controlled-release lipid formulations are particularly suitable.

BACKGROUND TO THE INVENTION

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable. Furthermore, in some circumstances, such as in the fitting of implants (e.g. joint replacements or oral implants) the area of desired action may not remain accessible for repeated administration. In such cases a single administration must provide active agent at a therapeutic level over the whole period during which activity is needed.

Various methods have been used and proposed for the sustained release of biologically active agents. Such methods include slow-release, orally administered compositions, such as coated tablets, formulations designed for gradual absorption, such as transdermal patches, and slow-release implants such as "sticks" or miniature syringe-type devices implanted under the skin.

One method by which the gradual release of a bioactive agent has been proposed is a so-called "depot" injection. In this method, a bioactive agent is formulated with carriers providing a gradual release of active agent over a period of a number of hours or days. These are often based upon a degrading matrix which gradually disperses in the body to release the active agent.

The most common of the established methods of depot injection relies upon a polymeric depot system. This is typically a biodegradable polymer such poly(lactic acid) (PLA) and/or poly(lactic-co-glycolic acid) (PLGA) and may be in the form of a solution in an organic solvent, a pre-polymer mixed with an initiator, encapsulated polymer particles or polymer microspheres. The polymer or polymer particles entrap the active agent and are gradually degraded releasing the agent by slow diffusion and/or as the matrix is absorbed. Examples of such systems include those described in U.S. Pat. No. 4,938,763, U.S. Pat. No. 5,480,656 and U.S. Pat. No. 6,113,943 and can result in delivery of active agents over a period of up to several months. These systems do, however, have a number of limitations including the complexity of manufacturing and difficulty in sterilising (especially the microspheres). The local irritation caused by the lactic and/or glycolic acid which is released at the injection site is also a noticeable drawback. There is also often quite a complex procedure to prepare the injection dose from the powder precursor, and this procedure must be conducted at the point of care just prior to administration.

From a drug delivery point of view, polymer depot compositions also have the disadvantage of accepting only relatively low drug loads and having a "burst/lag" release profile. The nature of the polymeric matrix, especially when applied as a solution or pre-polymer, causes an initial burst of drug release when the composition is first administered. This is followed by a period of low release, while the degradation of the matrix begins, followed finally by an increase in the release rate to the desired sustained profile. This burst/lag release profile can cause the in vivo concentration of active agent to burst above the functional window immediately following administration, and then drop back through the bottom of the functional window during the lag period before reaching a sustained functional concentration. Evidently, from a functional and toxicological point of view this burst/lag release profile is undesirable and could be dangerous. It may also limit the equilibrium concentration which can be provided due to the danger of adverse effects at the "peak" point.

A highly effective non-polymeric depot system was disclosed in WO2005/117830, in which a combination of a diacyl lipid or tocopherol, a phospholipid, and an oxygen containing organic solvent are combined to provide a controlled-release matrix. Such a system has considerable advantages, including a transition from low-viscosity to high-viscosity upon exposure to an aqueous environment, and the facility to provide a gradual release of active agent over a long period from a biocompatible and biodegradable composition. The disclosure of this document is hereby incorporated herein by reference.

Lipid-based systems such as that discussed above can also be used for other purposes by suitable choice of components, including the lipids, solvents and other additives used and their proportions. Such systems have advantages in being able to solubilise and deliver certain active agents which are otherwise difficult to dissolve for standard administration methods (e.g. WO2005/046642). Furthermore, the compositions can be selected to be bioadhesive, which allows delivery of active agents to a body surface over a sustained period (e.g. WO2006/075123).

The components of the delivery systems indicated above are highly biotolerable. Indeed, many of these are endogenous lipids, and can be beneficial even in the absence of an active pharmaceutical ingredient (API). This is particularly the case for bioadhesive formulations such as those indicated above, where the skin or mucosal surface may be soothed and/or protected by the composition itself, aside from any action by any API.

One limitation of previously known lipid controlled-release formulations is that many active agents and even the lipid components themselves can be susceptible to oxidative degradation. Various antioxidant compounds are known to offer some protection against this oxidative degradation but few of these are compatible with lipid based systems. It would therefore be of considerable advantage to provide an antioxidant/lipid combination which was compatible and provided protection of an active agent (such as an API) and/or of at least one lipid component against oxidative degradation.

The present inventors have now surprisingly established that thiol-containing antioxidants are unusually well suited to lipid formulations, and thus allow for such formulations to be stored for longer periods and/or have longer duration of action than other types of antioxidants previously tested.

BRIEF SUMMARY OF THE INVENTION

In a first aspect, the present invention therefore provides a formulation comprising:
i) a lipid matrix;
ii) at least one thiolated antioxidant;
iii) optionally and preferably at least one bioactive agent; and
iv) optionally at least one chelating agent.

The lipid matrix preferably comprises at least one phospholipid, at least one diacyl glycerol, at least one oxygenated organic solvent and optionally at least one fragmentation agent, as described herein below. It is preferable that optional bioactive agent (iii) dissolves or disperses in the remaining components to provide a low-viscosity mixture.

To the inventors' knowledge, it has not previously been suggested that thiolated antioxidants provide the surprising advantage in effectiveness in combination with lipid formulations.

In a further aspect, the present invention thus also provides a method for reducing oxidative degradation in a formulation comprising a lipid matrix and at least one bioactive agent, said method comprising adding at least one thiolated antioxidant and optionally at least one chelating agent. The various embodiments of this aspect are as described herein with respect to the formulation aspect.

In a yet further aspect, the present invention also provides the use of a thiolated antioxidant in the reduction of oxidative degradation in a formulation comprising a lipid matrix and at least one bioactive agent. The various embodiments of this aspect are as described herein with respect to the formulation aspect

DETAILED DESCRIPTION OF THE INVENTION

In all aspects, the present invention relates to the inclusion of a thiolated antioxidant into a lipid matrix for the purpose of reducing oxidative degradation of at least one component of the overall formulation. Any lipid based matrix may be used in the invention, and the effectiveness of the thiolated antioxidants may easily and routinely be tested by methods described herein, with particular reference to the Examples.

Lipid matrices are of particular utility in bioadhesive formulations (with or without bioactive agents such as APIs) and/or in controlled-release formulations whereby a bioactive agent (as described herein, including APIs) is formulated with the lipid matrix and thiolated antioxidant and is delivered to a subject over an extended period controlled by the nature of the lipid matrix and the phase behaviour of the formulation. In all cases, it is an advantage for the lipid matrix as formulated according to the present invention to undergo a change of phase following administration. In particular, it is preferable that the lipid matrix be in a low viscosity phase, such as lamellar or $L_2$ phase prior to administration and generate a non-lamellar phase, such as a liquid crystalline or $L_3$ phase after administration. Phase behaviour is further discussed below and applies to all aspects of the invention.

From a compositional point of view, it is an advantage if the lipid matrices of the present invention are highly biocompatible, and thus they should preferably comprise a high proportion of well tolerated components. In one embodiment, for example, the lipid matrix comprises less than 10% mono-acyl lipids (e.g. glycerol monooleate), because these are generally less well tolerated than diacyl lipids.

One preferred lipid matrix comprises:
a) at least one neutral lipid (e.g. diacyl lipid or tocopherol), preferably at least one diacyl glycerol and/or tocopherol;
b) at least one phospholipid;
c) at least one oxygenated organic solvent; and
d) optionally at least one fragmentation agent.

Such a matrix has a considerable advantage in that the components are typically very well tolerated by the subject, and furthermore, components and proportions can be selected to provide desirable phase behaviour.

Such suitable systems are described in detail in, for example, WO2005/117830 and are demonstrated in the examples included in that publication, which is incorporated herein by reference. In particular, details and proportions of components (a), (b) and (c) correspond to those described below and on pages 9 to 17 of WO2005/117830.

In this preferred lipid-based controlled-release matrix, weight ratios of components a:b may be from 5:95 to 95:5. Preferred ratios would generally be from 90:10 to 20:80 and more preferably from 85:15 to 30:70. The most preferred ratios of a:b are close to parity, especially 35:65 to 65:35, more preferably 42:58 to 58:42.

In any embodiment of the invention, and particularly with reference to the preferred lipid matrix, it is preferable that the formulation is low viscosity so as to allow ease of administration, and subsequently undergoes a phase change following administration. This allows the formulation to become more viscous and/or more bioadhesive after administration. Such a phase change may be brought about by a number of factors, but most commonly loss of solvent and/or absorption of water, either or both of which mechanisms may be brought about by exposure to an aqueous fluid.

Thus, the formulations of the invention in all aspects may employ a lipid matrix in the form of at least one non-lamellar phase, or may generate at least one non-lamellar phase upon exposure to an aqueous fluid. It is preferred that the lipid-based controlled-release matrix forms bulk or particulate ordered phases as described herein.

In all aspects of the present invention, the formulations are preferably low viscosity mixtures prior to administration. Herein, the term "low viscosity mixture" is used to indicate a mixture which may be readily administered to a subject and in particular readily administered by means of a standard syringe and needle arrangement. This may be indicated, for example by the ability to be dispensed from a 1 ml disposable syringe through a 19 awg, preferably 22 awg (or a 23 gauge) needle by manual pressure. In a particularly preferred embodiment, the low viscosity mixture should be a mixture capable of passing through a standard sterile filtration membrane such as a 0.22 µm syringe filter. In other preferred embodiments, a similar functional definition of a suitable viscosity can be defined as the viscosity of a formulation that can be sprayed using a compression pump or pressurized spray device using conventional spray equipment. A typical range of suitable viscosities is, for example, 0.1 to 5000 mPas, preferably 1 to 1000 mPas at 20° C.

It has been observed that, by the addition of small amounts of low viscosity solvent, as indicated herein, a very significant change in viscosity can be provided. For example, in some formulations, the addition of only 5% of a suitable solvent can reduce viscosity 100-fold and addition of 10% may reduce the viscosity up to 10,000 fold.

Particularly preferred examples of low viscosity mixtures are molecular solutions and/or isotropic phases such as L2 and/or L3 phases. As describe above, the L3 is a non-lamellar phase of interconnected sheets which has some phase structure but lacks the long-range order of a liquid crystalline phase. Unlike liquid crystalline phases, which are generally highly viscous, L3 phases are of lower viscosity. Obviously, mixtures of L3 phase and molecular solution and/or particles of L3 phase suspended in a bulk molecular solution of one or more components are also suitable. The L2 phase is the so-called "reversed micellar" phase or microemulsion. Most preferred low viscosity mixtures are molecular solutions, L3 phases and mixtures thereof. L2 phases are less preferred, except in the case of swollen $L_2$ phases. The $L_2$ phase as used herein throughout is preferably a "swollen" $L_2$ phase containing greater than 10 wt % of solvent (e.g. component c) having a viscosity reducing effect. This is in contrast to a "concentrated" or "unswollen" $L_2$ phase containing no solvent, or a lesser amount of solvent, or containing a solvent (or mixture) which does not provide the decrease in viscosity associated with the (typically oxygen-containing), low viscosity solvents specified herein.

Following exposure to an aqueous environment, it is preferable that the formulations of all aspects of the invention generate bulk or particulate ordered phases. Such phases are generally described herein as "non-lamellar". The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the L3 phase which comprises a multiply interconnected bi-continuous network of bilayer sheets which are non-lamellar but lack the long-range order of the liquid crystalline phases. Depending upon their curvature of the amphiphile sheets, these phases may be described as normal (mean curvature towards the apolar region) or reversed (mean curvature towards the polar region).

The non-lamellar liquid crystalline and $L_3$ phases are thermodynamically stable systems. That is to say, they are not simply a meta-stable state that will separate and/or reform into layers, lamellar phases or the like, but are the stable thermodynamic form of the lipid/solvent mixture. Bulk liquid crystalline phases are highly viscous and are advantageous for the formation of depot compositions wherein controlled release is desired over a prolonged period, especially following parenteral administration. $L_3$ and $L_2$ phases and dispersed particles of non-lamellar phases are typically lower viscosity and more suited to controlled release over shorter time periods, as well as to topical release at body surfaces, both internal and external.

In one preferred embodiment of the invention, the formulations form a bulk non-lamellar phase upon exposure to an aqueous fluid, particularly a body fluid. This typically occurs in vivo. Bulk non-lamellar phases are particularly suitable for forming long acting formulations, which act as a "depot" of active agent, potentially releasing this over a long period. This period may be controlled by adding relatively small quantities of the fragmentation agents (such as polysorbate 80) as described herein. 0 to 5% of fragmentation agent is typical for a bulk non-lamellar phase.

In an alternative embodiment, the formulations generate particles (such as colloidal) particles spontaneously upon exposure to an aqueous fluid, particularly a body fluid. This typically occurs in vivo. Fragmenting compositions may be used to generate shorter-acting depot compositions, or may be used over shorter periods to control the more rapid delivery of an active agent. Fragmenting or particulate non-lamellar phases are typically generated from compositions comprising a higher proportion of fragmentation agent (such as polysorbate 80), as described herein. 5 to 30% of fragmentation agent is typical for particulate non-lamellar phases. In all embodiments, all fragmentation agents discussed herein are suitable.

Component "(a)" as indicated herein is a neutral lipid component comprising a polar "head" group and also non-polar "tail" groups. Generally the head and tail portions of the lipid will be joined by an ester moiety but this attachment may be by means of an ether, an amide, a carbon-carbon bond or other attachment. Preferred polar head groups are non-ionic and include polyols such as glycerol, diglycerol and sugar moieties (such as inositol and glucosyl based moieties); and esters of polyols, such as acetate or succinate esters. Preferred polar groups are glycerol and diglycerol, especially glycerol.

In one preferred aspect, component (a) is a diacyl lipid in that it has two non-polar "tail" groups. This is generally preferable to the use of mono-acyl ("lyso") lipids because these are typically less well tolerated in vivo. The two non-polar groups may have the same or a differing number of carbon atoms and may each independently be saturated or unsaturated. Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include caproyl (C6:0), capryloyl (C8:0), capryl (C10:0), lauroyl (C12:0), myristoyl (C14:0), palmitoyl (C16:0), phytanoly (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable non-polar chains are palmitic, stearic, oleic and linoleic acids, particularly oleic acid.

The diacyl lipid, when used as all or part of component (a), may be synthetic or may be derived from a purified and/or chemically modified natural sources such as vegetable oils. Mixtures of any number of diacyl lipids may be used as component (a). Most preferably this component will include at least a portion of diacyl glycerol (DAG), especially glycerol dioleate (GDO). In one favoured embodiment, component (a) consists of or consists essentially of DAGs. These may be a single DAG or a mixture of DAGs. A highly preferred example is DAG comprising at least 50%, preferably at least 80% and even comprising substantially 100% GDO.

An alternative or additional highly preferred class of compounds for use as all or part of component (a) are tocopherols. As used herein, the term "a tocopherol" is used to indicate the non-ionic lipid tocopherol, often known as vitamin E, and/or any suitable salts and/or analogues thereof. Suitable analogues will be those providing the phase-behaviour, lack of toxicity, and phase change upon exposure to aqueous fluids, which characterise the compositions of the present invention. Such analogues will generally not form liquid crystalline phase structures as a pure compound in water. The most preferred of the tocopherols is tocopherol itself, having the structure below. Evidently, particularly where this is purified from a natural source, there may be a small proportion of non-tocopherol "contaminant" but this will not be sufficient to alter the advantageous phase-behaviour or lack of toxicity. Typically, a tocopherol will contain no more than 10% of non-tocopherol-analogue compounds, preferably no more than 5% and most preferably no more than 2% by weight.

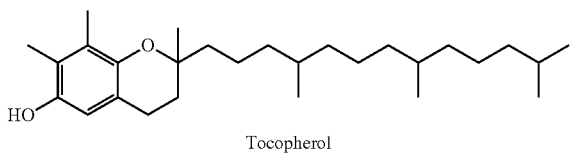 [SMILES: Cc1c(O)cc2c(c1C)OC(C)(CCCC(C)CCCC(C)CCCC(C)C)CC2]

Tocopherol

In a further advantageous embodiment of the invention, component (a) consists essentially of tocopherols, in particular tocopherol as shown above.

A preferred combination of constituents for component (a) is a mixture of at least one DAG (e.g. GDO) with at least one tocopherol. Such mixtures include 2:98 to 98:2 by weight tocopherol:GDO, e.g. 10:90 to 90:10 tocopherol:GDO and especially 20:80 to 80:20 of these compounds. Similar mixtures of tocopherol with other DAGs are also suitable.

Component "(b)" in the present invention is at least one phospholipid. As with component (a), this component comprises a polar head group and at least one non-polar tail group. The difference between components (a) and (b) lies principally in the polar group. The non-polar portions may thus suitably be derived from the fatty acids or corresponding alcohols considered above for component (a). It will typically be the case that the phospholipid will contain two non-polar groups, although one or more constituents of this component may have one non-polar moiety. Where more than one non-polar group is present these may be the same or different.

Preferred phospholipid polar "head" groups include phosphocholine, phosphoethanolamine, phosphoserine and phosphoinositol. Most preferred is phosphocholine, making phosphatidyl choline (PC) the preferred constituent of component (b). In a preferred embodiment, component (b) thus consists of at least 50% PC, preferably at least 70% PC and most preferably at least 80% PC. Component (b) may consist essentially of PC.

The phospholipid portion, even more suitably than any diacyl lipid portion, may be derived from a natural source. Suitable sources of phospholipids include egg, heart (e.g. bovine), brain, liver (e.g. bovine) and plant sources including soybean. Such sources may provide one or more constituents of component (b), which may comprise any mixture of phospholipids.

Because the formulations of the invention are to be administered to a subject for the controlled release of an active agent, it is preferable that the components (a) and (b) are biocompatible. In this regard, it is preferable to use, for example, diacyl lipids and phospholipids rather than mono-acyl (lyso) compounds. A notable exception to this is tocopherol, as described above. Although having only one alkyl chain, this is not a "lyso" lipid in the conventional sense and is not encompassed by "lyso" lipids, or "monoacyl" lipids as used herein. The nature of tocopherol as a well tolerated essential vitamin makes it highly biocompatible.

Two particularly preferred combinations of components (a) and (b) are GDO with PC and tocopherol with PC, especially in the region 30-90 wt % GDO/tocopherol, 10-60 wt % PC and 1-30% solvent (especially ethanol, benzyl alcohol, n-methyl pyrrolidone (NMP) and/or isopropanol).

In addition to amphiphilic components (a) and (b), the preferred lipid matrices of the invention may also contain additional amphiphilic components, although it is preferred that these are at relatively low levels. In one embodiment of the invention, the pre-formulation contains up to 10% (by weight of components (a) and (b)) of a charged amphiphile, particularly an anionic amphiphile such as a fatty acid or anionic phospholipid. Preferred fatty acids for this purpose include caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable fatty acids are palmitic, stearic, oleic and linoleic acids, particularly oleic acid. Preferred anionic phospholipids include phosphatidylglycerol (PG), phosphatidylserine (PS) and phosphatidic acid (PA). Preferable phospholipids are dioleoylphosphatidylglycerol (DOPG), palmitoyloleoylphosphatidylglycerol (POPG), dioleoylphosphatidylserine (DOPS), dioleoylphosphatidic acid (DOPA), soy-derived phosphatidylglycerol and egg-derived phosphatidylglycerol, particularly DOPG and POPG. It is particularly advantageous that these components be used in combination with a cationic peptide active agent (see below). The combination of an anionic lipid and a cationic peptide is believed to provide a sustained release composition of particular value. This may in part be due to increased protection of the peptide from the degradative enzymes present in vivo.

Optional but preferable component "(c)" of the lipid-based controlled-release matrix is an oxygen containing organic solvent. Because the formulations are for use in contact with an aqueous fluid, and particularly a body-fluid (e.g. in vivo), it is desirable that this solvent be tolerable to the subject and be capable of mixing with the aqueous fluid, and/or diffusing or dissolving out of the pre-formulation into the aqueous fluid. Solvents having at least moderate water solubility are thus preferred.

Typical solvents suitable for use as component (c) include at least one solvent selected from alcohols, ketones, esters (including lactones), ethers, amides and sulphoxides. Examples of suitable alcohols include ethanol, isopropanol, benzyl alcohol and glycerol formal. Monools are preferred to diols and polyols. Where diols or polyols are used, this is preferably in combination with an at least equal amount of monool or other preferred solvent. Examples of ketones include acetone, and propylene carbonate. Suitable ethers include diethylether, glycofurol, diethylene glycol monoethyl ether, dimethylisobarbide, and polyethylene glycols. Suitable esters include ethyl acetate, benzyl benzoate and isopropyl acetate and dimethyl sulphide is as suitable sulphide solvent. Suitable amides include NMP, 2-pyrrolidone, and dimethylacetamide (DMA), and sulphoxides include dimethylsulphoxide (DMSO). Less preferred solvents include dimethyl isosorbide, tetrahydrofurfuryl alcohol, diglyme and ethyl lactate.

The solvent component (c) will generally be at least partially lost upon in vivo formation of the depot composition, will evaporate, or will be diluted by absorption of water from the surrounding air and/or tissue. It is preferable, therefore, that component (c) be at least to some extent water miscible or dispersible, and at least should not repel water to the extent that water absorption is prevented. In this respect also, oxygen containing solvents with relatively small numbers of carbon atoms (for example up to 10 carbons, preferably up to 8 carbons) are preferred. Obviously, where more oxygens are present a solvent will tend to remain soluble in water with a larger number of carbon atoms. The carbon to heteroatom (e.g. N, O, preferably oxygen) ratio will thus often be around 1:1 to 6:1, preferably 2:1 to 4:1. Where a solvent with a ratio outside one of these preferred ranges is used then this will preferably be no more than 75%, preferably no more than 50%, in combination with a preferred solvent (such as ethanol). This may be used, for example, to decrease the rate of evaporation of the solvent from the pre-formulation to control the rate of liquid crystalline depot formation.

The amount of component (c), where present in the formulations of the invention and in the lipid-based controlled-release matrix will be at least sufficient to provide a low viscosity mixture (e.g. a molecular solution, see above) of all components, and will be easily determined for any particular combination of components by standard methods in view of the present disclosure. The phase behaviour itself may be analysed by techniques such as visual observation in combination with polarized light microscopy, nuclear magnetic resonance, and cryo-transmission electron microscopy (cryo-TEM) to look for solutions, L2 or L3 phases, or liquid crystalline phases. Viscosity may be measured directly by standard means. As described above, an appropriate practical viscosity is that which can effectively be syringed and particularly sterile filtered. This will be assessed easily as indicated herein. The maximum amount of component (c) to be included will depend upon the exact application of the formulation but generally the desired properties will be provided by any amount forming a low viscosity mixture (e.g. a molecular solution, see above) and/or a solution with sufficiently low viscosity. Because the administration of unnecessarily large amounts of solvent to a subject is generally undesirable the amount of component (c) will typically be limited to no more than ten times (e.g. three times) the minimum amount required to form a low viscosity mixture, preferably no more than five times and most preferably no more than twice this amount. The composition of the present invention may, however, contain a greater quantity of solvent than would be acceptable in an immediate dosage composition. This is because the process by which the active agents are slowly released (e.g. formation of shells of liquid crystalline phase as described herein) also serve to retard the passage of solvent from the composition. As a result, the solvent is released over some time (e.g. minutes or hours) rather than instantaneously and so can be better tolerated by the body.

Because viscosity is a highly significant factor in administering compositions by injection or spraying, it is preferred that the solvent be itself of very low viscosity. The viscosity of the "low viscosity" solvent component (c) (single solvent or mixture) should typically be no more than 18 mPas at 20° C. This is preferably no more than 15 mPas, more preferably no more than 10 mPas and most preferably no more than 7 mPas at 20° C. Furthermore, the solvent should be suitable for lowering the viscosity of the matrix, and any other components (e.g. active agent) in the mixture. Ethanol is particularly preferred as suitable in all of these respects.

Higher proportions of solvent may also be used for non-parenteral (e.g. topical) applications, especially to body surfaces, where the solvent will be lost by evaporation rather than absorbed into the body. For such applications up to 100 times the minimum amount of solvent may be used (e.g. up to 95% by weight of the composition, preferably up to 80% by weight and more preferably up to 50% by weight), especially where a very thin layer of the resulting non-parenteral composition is desired.

As a general guide, the weight of component c will typically be around 0.5 to 50% of the total weight of the (a)-(b)-(c) (and (d) where present) solution. This proportion is preferably (especially for injectable compositions) 2 to 30% and more preferably 5 to 20% by weight.

The formulations of the present invention typically do not contain significant amounts of water. Because it is essentially impossible to remove every trace of water from a lipid composition, this is to be taken as indicating that only such minimal trace of water exists as cannot readily be removed. Such an amount will generally be less than 1% by weight, preferably less that 0.5% by the weight of the pre-formulation. In one preferred aspect, the formulations of the invention do not contain glycerol, ethylene glycol or propylene glycol and contain no more than a trace of water, as just described. Alternatively, propylene glycol may be present as the sole solvent, or as one component of the solvent.

There is a certain embodiment of the present invention in which higher proportions of water may be tolerated. This is where water is present as a part of the solvent component in combination with an additional water-miscible component (c) (single solvent or mixture). In this embodiment, up to 20%, preferably up to 10 wt % water may be present providing that at least 3 wt %, preferably at least 5% and more preferably at least 7 wt % component (c) is also present, that component (c) is water miscible, and that the resulting pre-formulation remains non-viscous and thus does not form a liquid crystalline phase. Generally the weight ratio between organic solvent component (c) and water will be between 20:80 and 80:20, preferably 30:70 to 70:30 and more preferably 35:65 to 65:35. In one embodiment the proportion is at least 50% solvent. Most suitable solvents of use with water in this aspect of the invention include ethanol, isopropyl alcohol, NMP, acetone and ethyl acetate.

As optional but preferable fragmentation agent component (d) can function any amphiphile capable of serving as a fragmentation agent with the selected components (a) and (b) (and (c), where present). A fragmentation agent is a (pure or mixed) agent which allows the composition comprising components (a) and (b) to form (by self-dispersion or by the input of energy, such as by shearing or sonication) structured particles, as described herein. Particularly suitable particles are e.g. non-lamellar, especially liquid crystalline, $L_2$ or $L_3$. Non lamellar phases are described in greater detail herein above.

There are a number of different molecular classes that are suitable as fragmentation agents in the present invention. These include;
1) Polymeric agents: Poloxamers (preferably Pluronic® F127, Pluronic® F68, Pluronic® F108 Pluronic® L44), 2-Methacryloyloxyethyl phosphorylcholine n-butyl methacrylate co-block polymers (such as PUREBRIGHT MB-37-50T and PUREBRIGHT MB-37-100T from NOF Corp.), pegylated sorbitan fatty acid esters (polysorbates, particularly Polysorbate 80), PEGylated surfactants (e.g. Solutol HS15 from BASF), pegylated castor oil derivatives (e.g. Cremophor EL, Cremophor RH40), pegylated fatty acids (e.g. PEG-oleate), pegylated phospholipids (including DOPE-PEG(2000), DOPE-PEG(5000) and DSPE-PEG (5000)), polyglycerin(PG)-phospholipids (such as DSPE-PG, for example, SUNBRIGHT DSPE-PG8G from NOF Corp., DOPE-PG), pegylated oligoalkylsorbitols (such as PEG-60 Sorbitoltetraoleate, e.g. GO-460V from Nikko Chemicals), pegylated glyceryl fatty acid esters (e.g. TMGO-15 (Nikko Chemicals)), pegylated tocopherols such as d-alpha tocopheryl polyethylene glycol 1000 succinate (Vitamin E TPGS (Eastman)) and pegylated alkyl ethers;

2) Polyol surfactants: sugar derived alkyl esters (such as sucrose laurate and sucrose oleate), sugar derived alkyl ethers (e.g. octyl glucoside);

3) Proteins: including casein, sodium caseinate, lysozyme;

4) Anionic surfactants: Carboxylates of fatty acids (especially sodium oleate, sodium palmitate, sodium stearate, sodium myristate), alkyl sulfates (such as sodium dodecyl sulphate (SDS)); and 5) Cationic surfactants: alkyl ammonium salts (including dodecyl trimethyl ammonium bromide (DTAB), cetyl trimethyl ammonium bromide (CTAB) and oleyl ammonium chloride).

Generally, in the present invention, protein fragmentation agents, such as those described in (3) above are less preferred. Class (1) as described above also includes fragmentation agents that are highly suitable for this purpose.

The majority of the (d)-components form normal micellar (L1) phases on contact with excess water. However, the components need not form micelles to function as fragmentation agents. The effective functioning of a fragmentation agent will easily be tested by a skilled worker by preparing appropriate compositions and conducting simple tests as illustrated in the Examples herein, and also by reference to WO2006/013369 (particularly the Examples), the disclosure of which is incorporated herein by reference.

Where component (d) is present, the components (a), (b) and (d) will typically be present in the following proportions (where a, b and d are the weights of components (a), (b) and (d) respectively); d/(a+b+d) is between 0.01 and 0.3. Compositions within this range have a high tendency to self-disperse or to form stable particles following dispersion with or without energy input. It is preferred, especially where it is desired to provide self-dispersion and greatest particle size control that the proportions of (a), (b) and (d) are such that a/(a+b+d) is between 0.25 (e.g. 0.35) and 0.80 (e.g. 0.75), more preferably 0.35 (e.g. 0.4) and 0.75 (e.g. 0.65) and d/(a+b+d) is between 0.03 and 0.25 (e.g. 0.2) (where a, b and d are the weights of components (a), (b) and (d) respectively).

In one embodiment, the surfactant is one of types 1, 3, 4 or 5, shown above, most preferably a polymer surfactant.

As with all components indicated explicitly or implicitly herein as optional, components (c) and (d) may each independently be present or absent.

One of the key components of the present invention is the thiolated antioxidant. Like essentially all organic molecules, lipids and biologically active agents are thermodynamically unstable to oxidation. As a result, many lipid formulations, including those comprising bioactive agents such as APIs are susceptible to degradation upon storage, especially by oxidation.

Unfortunately, many common antioxidants are not highly compatible with lipid systems. Indeed, the present inventors have surprisingly established that some antioxidants commonly used in previous systems can cause increased degradation of active agents in a lipid system. This applies particularly to peptide active agents. The present inventors have therefore analysed a variety of potential antioxidant compounds and classes for use with lipid based matrix systems and have surprisingly found that one particularly class of antioxidants is unusually well suited for use in these systems.

The present inventors have now established that thiolated antioxidants, particularly mono-thioglycerol (MTG) and cysteine analogues such as N-acetyl cysteine, are highly effective in lipid based systems, and thus in the present invention the antioxidant component is a thiolated antioxidant, preferably thiolated sugar, thiolated amino acid, a thiolated amino ester, or a thiolated polyol. Mono-thioglycerol, N-acetyl cysteine or cysteine are preferred thiolated antioxidants.

The antioxidant component is generally included in the range 0.01 to 2.0% by weight of the total composition (formulation). This is most preferably 0.05 to 1.0%, and around 0.2 to 0.5% of antioxidant (particularly MTG) is particularly preferred, especially in combination with the other preferred components and ranges indicated herein above and below.

The reason for the utility of thiolated antioxidants in general and MTG in particular is not known. Without being bound by theory, it is believed that MTG acts as an effective chain-breaking donating antioxidant according to established mechanisms whereby peroxyl radicals (ROO•) are neutralized. Their quenching by the thiolated antioxidant breaks the cycle of further oxidative degradation. Thiols such as MTG and N-acetyl cysteine may also regenerate certain components from their oxidized forms.

Stability data using a number of different antioxidants shown in the Examples below demonstrate that thiolated antioxidants are surprisingly more efficient than other antioxidants in suppressing the oxidative degradation of bioactive agents. This effect is outlined in the Examples and tables below and in the attached Figures.

The present inventors have additionally established that the combination of a thiolated antioxidant compound and a chelating agent provides a highly effective combination in stabilising the lipid based compositions of the invention. In all aspects of the invention, the antioxidant component may thus be supplemented with a chelator. Suitable chelating agents include any poly-dentate (including bi-dentate) ligand, including poly-acids, poly-amides, poly-amines and poly-ethers. Many metal-chelating ligands are known to those skilled in the art, and will be suitable for use in the present invention. Preferred chelating agents include diethylenetriaminepentaacetic acid (DTPA), ethylenediamine tetraacetic acid (EDTA) and the corresponding sodium, disodium and calcium disodium salts of EDTA. Citric acid, and its biologically tolerable salts (e.g. sodium, calcium, potassium and/or magnesium salts) also functions as a chelator and could be used as the chelating agent in the method of the present invention. The amounts of chelator required may be quite small, and thus citric acid may act as a chelator at concentrations equal to or below that required to have a lipid-soluble-acid effect (see below). In an alternative embodiment, citric acid may be excluded from the pre-formulations of the invention.

Without being bound by theory, it is thought that the metal chelating nature of the chelating agent serves to compliment the chain-breaking donating antioxidant property of the thiolated antioxidant, thus serving together to reduce the formation of oxygenated radical species, and quench those that do form.

The chelating agent is generally included in the range 0.005 to 1.0% by weight of the total composition (formulation). This is most preferably 0.01 to 0.8%, and around 0.02 to 0.5% of chelating agent is particularly preferred, especially in combination with the other preferred components and ranges indicated herein above.

One useful embodiment of the present invention combines an antioxidant, as described herein, a chelating agent, and a lipid composition which forms particles of non-lamellar phase upon exposure to a body fluid. Such compositions typically comprise a fragmentation agent such as polysorbate 80 (P80) and typical lipid components are described herein. MTG, EDTA, GDO, PC and P80 form a highly preferred combination, along with an optional organic solvent such as ethanol and/or propylene glycol. The addition of citric acid, or use of citric acid in place of EDTA is also a valuable embodiment. The amounts of each component which are suitable are those discussed herein.

An optional component of the formulations of the present invention is a bioactive agent. In one embodiment, the lipid matrices stabilised by thiolated antioxidant may be used without any additional bioactive agent, and in particular without any active pharmaceutical agent (API), for example for their soothing and/or protective properties at biological surfaces such as mucosal surfaces. In an alternative and preferred embodiment, however, one or more bioactive agent is included in the formulations.

As used herein, the term "bioactive agent" (described equivalently as "active agent" herein) may be any compound having a desired biological or physiological effect, such as a protein, drug, antigen, nutrient, cosmetic, fragrance, flavouring, diagnostic, pharmaceutical, vitamin, or dietary agent and will be formulated at a level sufficient to provide an in vivo concentration at a functional level (including local concentrations for topical compositions). Under some circumstances one or more of components of the lipid matrix i) (e.g. components (a), (b), (c) and/or (d)) may also be an active agent, although it is preferred that the optional bioactive agent (iii) should not be one of these components (e.g. should not be a component of the lipid matrix). Most preferred active agents are pharmaceutical agents (e.g. APIs) including drugs, vaccines, and diagnostic agents.

Drug agents that may be delivered by the present invention and formulated therewith include drugs which act on cells and receptors, peripheral nerves, adrenergic receptors, cholinergic receptors, the skeletal muscles, the cardiovascular system, smooth muscles, the blood circulation system, endocrine and hormone system, blood circulatory system, synoptic sites, neuroeffector junctional sites, the immunological system, the reproductive system, the skeletal system, autacoid system, the alimentary and excretory systems, the histamine system, and the central nervous system.

Examples of drugs which may be formulated in the compositions of the present invention include, but are not limited to, antibacterial agents such as β-lactams or macrocyclic peptide antibiotics, anti fungal agents such as polyene macrolides (e.g. amphotericin B) or azole antifungals, anticancer and/or anti viral drugs such as nucleoside analogues, paclitaxel and derivatives thereof, docetaxel and derivatives thereof, anti inflammatorys, such as non-steroidal anti inflammatory drugs and corticosteroids, cardiovascular drugs including cholesterol lowering and blood-pressure lowing agents, analgesics, antipsychotics and antidepressants including seritonin uptake inhibitors, prostaglandins and derivatives, vaccines, and bone modulators. Diagnostic agents include radionuclide labelled compounds and contrast agents including X-ray, ultrasound and MRI contrast enhancing agents. Nutrients include vitamins, coenzymes, dietary supplements, etc.

Particularly suitable active agents include those which would normally have a short residence time in the body due to rapid breakdown or excretion, those with poor oral bioavailability and particularly those which are susceptible to oxidative degradation. These include peptide, protein and nucleic acid based active agents, hormones and other naturally occurring agents in their native or modified forms. In one highly preferred embodiment of the present invention, such agents are administered in the form of a lipid depot composition formed, for example, from the preferred lipid matrices described herein. In this way, the active agents are provided at a sustained level for a length of time which may stretch to days, weeks or even several months in spite of having rapid clearance rates, and can be kept at a desired dosage level for an extended period due to effective protection from oxidative degradation. This offers obvious advantages in terms of dosage stability and patient compliance over dosing multiple times each day for the same period. In one preferred embodiment, the active agent thus has a biological half life (upon entry into the blood stream) of less than 1 day, preferably less than 12 hours and more preferably less than 6 hours. In some cases this may be as low as 1-3 hours or less. Suitable agents are also those with poor oral bioavailability relative to that achieved by injection, for where the active agent also or alternatively has a bioavailability of below 0.1%, especially below 0.05% in oral formulations.

Peptide and protein based active agents include human and veterinary drugs selected from the group consisting of adrenocorticotropic hormone (ACTH) and its fragments, angiotensin and its related peptides, antibodies and their fragments, antigens and their fragments, atrial natriuretic peptides, bioadhesive peptides, Bradykinins and their related peptides, calcitonins and their related peptides, cell surface receptor protein fragments, chemotactic peptides, cyclosporins, cytokines, Dynorphins and their related peptides, endorphins and P-lidotropin fragments, enkephalin and their related proteins, enzyme inhibitors, immunostimulating peptides and polyaminoacids, fibronectin fragments and their related peptides, gastrointestinal peptides, gonadotrophin-releasing hormone (GnRH) agonists and antagonist, glucagon, glucagon-like peptides 1 and 2 (GLP-1 and GLP-2) (plus other peptide GLP-1 and GLP-2 receptor agonists), growth hormone releasing peptides, immunostimulating peptides, insulins and insulin-like growth factors, interleukins, luthenizing hormone releasing hormones (LHRH) and their related peptides, melanocyte stimulating hormones and their related peptides, nuclear localization signal related peptides, neurotensins and their related peptides, neurotransmitter peptides, opioid peptides, oxytocins, vasopressins and their related peptides, parathyroid hormone and its fragments, protein kinases and their related peptides, somatostatins and their related peptides, substance P and its related peptides, transforming growth factors (TGF) and their related peptides, tumor necrosis factor fragments, toxins and toxoids and functional peptides such as anticancer peptides including angiostatins, antihypertension peptides, anti-blood clotting peptides, and antimicrobial peptides; selected from the group consisting of proteins such as immunoglobulins, angiogenins, bone morphogenic proteins, chemokines, colony stimulating factors (CSF), cytokines, growth factors, interferons (Type I and II), interleukins, leptins, leukaemia inhibitory factors, stem cell factors, transforming growth factors and tumor necrosis factors.

A further considerable advantage of the depot compositions of the present invention is that active agents are released gradually over long periods without the need for repeated dosing. The compositions are thus highly suitable for situations where patient compliance is difficult, unreliable or where a level dosage is highly important, such as mood-altering actives, those actives with a narrow therapeutic window, and those administered to children or to people who's lifestyle is incompatible with a reliable dosing regime. The compositions of the invention are also useful for "lifestyle" APIs where the inconvenience of repeated dosing might outweigh the benefit of the API. Particular classes of APIs for which this aspect offers a particular advantage include contraceptives, hormones (including contraceptive hormones and particularly hormones used in children such as growth hormone), anti-addictive agents, supplements such as vitamin or mineral supplements, anti-depressants and anticonvulsants.

Cationic peptides are suitable for use, particularly in embodiments where a portion of the lipid matrix part of the formulation comprises an anionic amphiphile such as a fatty acid or anionic phospholipid. In this embodiment, preferred peptides include calcitonin, oxytocin, interferon-beta and -gamma, interleukins 4, 5, 7 and 8 and other peptides having an isoelectric point above pH 7, especially above pH 8.

Because the antioxidants used in the present invention are slightly reducing, it is preferred that the active agents used in the method of the invention should not be susceptible to permanent inactivation by reduction. Thus, for example, peptide active agents are preferably those which are not reduction-sensitive. Typically, peptides (including proteins) which form one or more disulphide linkages may be susceptible to reductive inactivation, and so are less preferred. In some cases, however, the necessary cross-links re-form spontaneously upon exposure to the normal oxidative environment in vivo, and in such cases the peptide agents remain suitable for use in the present invention.

Where present, the amount of bioactive agent to be formulated in the present invention will depend upon the functional dose and the period during which the composition formed upon administration is to provide sustained release. Typically, the dose formulated for a particular agent will be around the equivalent of the normal daily dose multiplied by the number of days the formulation is to provide release. This amount can be tailored to take into account any adverse effects of a large dose at the beginning of treatment, as this will generally be the maximum dose used. The precise amount suitable in any case can readily be determined by suitable experimentation in view of the present disclosure.

In one embodiment, the pre-formulations of the present invention will be administered parenterally. This administration will generally not be an intra-vascular method but will preferably be subcutaneous intracavitary or intramuscular or subcutaneous. Typically the administration will be by injection, which term is used herein to indicate any method in which the formulation is passed through the skin or mucosal surface, such as by needle, catheter or needleless injector.

In parenteral (especially subcutaneous) depot precursor formulation, preferred active agents are those suitable for systemic administration including antibacterials (including amicacin, monocycline and doxycycline), local and systemic analgesics (including bupivacain, tramadol, fentanyl, morphine, hydromorphone, methadone, buprenorphine, oxycodone, codeine, asperine, acetaminophen), NSAIDS (such as ibuprofene, naproxene, keteprofene, indomethansine, sulindac, tolmethin, salysylic acids such as salisylamide, diflunisal), Cox1 or Cox2 inhibitors (such as celecoxib, rofecoxib, valdecoxib), anticancer agents (including octreotide, lanreotide, buserelin, leuprorelin, goserelin, triptorelin, avorelin, deslorein, abarelix, degarelix, fulvestrant, interferon alpha, interferon beta, darbepoetin alpha, epoetin alpha, beta, delta, docetaxel and paclitaxel), antipsychotics (like bromperidol, risperidone, olanzapine, iloperidone, paliperadone, pipotiazine and zuclopenthixol), antivirals, anticonvulsants (for instance tiagabine topiramate or gabapentin) or nicotine, hormones (such as testosterone, and testosterone undecanoate, medroxyprogesterone, estradiol) growth hormones (like human growth hormone), and growth factors (like granulocyte macrophage colony-stimulating factor). Peptide active agents such as glucagon and opiate active agents such as Buprenorphine are particularly preferred active agents in all embodiments of the present invention.

In an alternative embodiment, the formulations of the present invention may form non-parenteral depots where the active agent is slowly released at a body surface. It is especially important in this embodiment that the formulations of the invention and/or the (preferably non-lamellar, e.g. liquid crystalline) depot compositions formed therefrom should preferably be bioadhesive. That is to say that the compositions should coat the surface to which they are applied and/or upon which they form as appropriate and should remain even when this surface is subject to a flow of air or liquid and/or when the surface is rubbed. It is particularly preferable that the depot compositions formed should be stable to rinsing with water. For example, a small volume of depot precursor may be applied to a body surface and be exposed to a flow of five hundred times its own volume of water per minute for 5 minutes. After this treatment, the composition can be considered bioadhesive if less than 50% of the bioactive agent has been lost. Preferably this level of loss will be matched when water equaling 1000 times and more preferably 10 000 times the volume of the composition is flowed past per minute for five, or preferably 10, minutes.

Although the non-parenteral compositions of the present invention may absorb some or all of the water needed to form a liquid crystalline phase structure from the biological surfaces with which they are contacted, some additional water may also be absorbed from the surrounding air. In particular, where a thin layer of high surface area is formed then the affinity of the composition for water may be sufficient for it to form a liquid crystalline phase structure by contact with the water in the air. The "aqueous fluid" referred to herein is thus, at least partially, air containing some moisture in this embodiment.

Non-parenteral depot compositions will typically be generated by applying the formulations described herein topically to a body surface or to a natural or artificially generated body cavity and/or to the surface of an implant. This application may be by direct application of liquid such as by spraying, dipping, rinsing, application from a pad or ball roller, intra-cavity injection (e.g to an open cavity with or without the use of a needle), painting, dropping (especially into the eyes) and similar methods. A highly effective method is aerosol or pump spraying, and this requires that the viscosity of the pre-formulation be as low as possible and is thus highly suited to the preferred lipid compositions of the invention. Non-parenteral depots may, however, be used to administer systemic agents e.g. transmucosally or transdermally.

Non-parenteral depots may also be used for application to surfaces, particularly of implants and materials which will be in contact with the body or a body part or fluid. Devices such as implants, catheters, stents and the like may thus be treated e.g. by dipping or spraying with the formulations of the invention, which will form a robust layer to reduce the introduction of infection. Anti-infective actives are particularly suited to this aspect.

A further advantageous component which may be included in the formulations of the present invention is a lipid soluble acid. The optional "lipid soluble acid" component is generally a low molecular weight compound which would form an acidic solution in an aqueous medium (i.e. in water). Although referred to as an "acid" herein, and acting as an acid in aqueous solutions, this component does not generally act as a typical acid in the pre-formulations of the invention, because these are lipid-based and thus generally non-aqueous. In one embodiment, such a lipid soluble acid has a molecular weight of less than 500 amu, e.g. less than 300 amu and less than 200 amu. Organic and mineral acids are useful lipid soluble acids for purposes of the present invention, especially those having low molecular weight as indicated. The lipid soluble acids will generally be those having a pKa of lower than 5, such as lower than 4.7 and lower than 4.5. The acids must also be suitable for dissolution at the required level in the chosen matrix system. As the matrices are generally hydrophobic or amphiphilic, suitable acids are referred to herein as "lipid soluble". Because the lipid soluble acids are often administered as part of a parenteral drug-release system, biocompatibility in the relevant quantities is also necessary. Suitable lipid soluble acids include those selected from citric acid, benzoic acid, sulphonic acids (e.g. methane sulphonic acid, benzene sulphonic acid or toluene sulphonic acid) and hydrohalic acids (e.g. hydrochloric acid, hydrobromic acid or hydroiodic acid). In various embodiments, lipid soluble acids are citric acid, methane sulphonic acid, benzene sulphonic acid, benzoic acid, toluene sulphonic acid and HCl. Citric acid and benzoic acid are highly preferred and preferably used in combination with PC (soy and/or DOPC), GDO, ethanol and optionally PG. This use in combination may be in the component ratios as described herein above.

In one alternative embodiment of the invention, the lipid soluble acid is not a hydrohalic acid (e.g. not HCl, not HBr and/or not HI). In this embodiment, the lipid soluble acid may be, in some embodiments, benzoic acid, citric acid or a sulphonic acid.

In another alternative embodiment of the invention, the lipid soluble acid is not one or more of acetic acid, or ascorbic acid. In one embodiment, the acid may be citric acid. In an alternative embodiment, the acid is an acid other than citric acid.

Typically, the acid functionality will be the only or the dominant functional group in an organic lipid-soluble acid for use in the present invention, and thus, the acid will optionally not be a fatty acid, (e.g. having a carbon chain greater than $C_6$), an amino acid, or a poly acid, especially a chelating poly-acid such as EDTA. Thus, for example, in one embodiment the acid may be an organic acid having one or more, but typically no more than 5 acid groups, often no more than four and usually no more than three acid groups. Thus, mono-, di- or tri-acids are preferred.

The lipid soluble acids are referred to herein as "acids" and in one aspect they are formulated as at least essentially consisting of the acid in free acid form. In an alternative aspect, however, the lipid soluble acid may be the salt of the corresponding acid as described herein, wherein the counter-ion is a physiologically acceptable ion such as an alkali-metal or alkaline earth metal cation, an ammonium ion or a substituted ammonium ion. A mixture of such ions is also suitable. In one corresponding embodiment, the counter-ion is the cation of the active agent, such as a peptide active agent (e.g. a glucagon ion), or a mixture of ions including the cation of the active agent.

Without being bound by theory, it is believed that the ions of the lipid soluble acids serve to stabilise the active agent component. Because the compositions are typically essentially free of water, the aqueous hydrogen ion concentration, which is the normal basis of pH does not directly apply, and the lipid soluble acids must have an additional effect in these systems. It is certainly observed that active agent components can be formulated at higher concentrations and/or can be more stable in the compositions of the present invention in the presence of the acid component. In this context, stability is the physical stability of the compositions as well as the chemical stability of the active agent.

In some embodiments, the lipid soluble acid can be highly beneficial in combination with a thiolated antioxidant for stabilising an active agent.

In all aspects of the invention, the lipid soluble acid, where present, is present at a molar ratio of active agent to lipid soluble acid of 1:1 to 1:5000, for example 1:100 to 1:1000, preferably 1:100 to 1:300 or from 1:1 to 1:30, preferably 1:1 to 1:20, and most preferably 1:2 to 1:10. Because typical lipid soluble acids are of lower molecular weight than typical peptide active agents, the proportion by weight of lipid soluble acid may be relatively small. For example, with a small molecular weight pH adjuster (e.g. less than 500 amu), 0.01 to 5% of the composition may be lipid soluble acid, such as 0.05 to 2%. Either the absence of acid component, or the presence of citric acid at 0.2 to 2% by weight of the complete formulation is typical.

From a weight point of view, the amount of lipid soluble active agent may depend upon the molecular weight of the acid and the active agent used, and can be calculated from the molar ratios indicated herein. For example, with a peptide active agent of molecular weight 3000-4000 amu, and an acid component of molecular weight 150 to 250 amu, the weight of lipid soluble acid in the formulation may be from around 1:1 to 30:1 of acid:active agent. This will usually be 1:1 to 20:1, more preferably 5:1 to 15:1.

In one embodiment of the present invention, the lipid soluble acid may act to limit aggregation of the active agent, such as a peptide active agent. The thiol based antioxidants such as MTG are particularly effective in combination with the typical acid, including citric acid and benzoic acid. A synergistic effect may develop from these two components when used as indicated herein. In particular, the anti-oxidising and anti-aggregation effects of the respective components may act synergistically in the preservation of active agent in the lipid vehicle as set out herein. Furthermore, the metal chelating effect of a chelating agent such as EDTA may act synergistically with the thiol-based antioxidant and/or the lipid soluble acid to preserve the active agent and/or lipid by preventing the generation and/or propagation of radicals.

The resistance to oxidation provided in the formulations of the present invention has two primary advantages for practical formulations. Firstly, those compositions formulated to release an active agent over long periods of time do so more efficiently and effectively if that active agent is not oxidised during the release period (e.g. while at least a part of the dose of active agent remains trapped within the structure generated when the formulation was administered). Secondly, oxidation resistance is advantageous because the formulations will then have greater stability to transport and storage. It is necessary that any formulation which is to be generated in large quantities, packaged, transported, stored and/or distributed has a certain stable lifetime. This should preferably be at least a month, more preferably at least 3 months and most preferably at least 6 months. In many cases, this can only be achieved by providing the components in a separated form, such that they must then be combined shortly or immediately before administration. This procedure can be complex and in any case places an additional burden on the practitioner or user to prepare the composition.

The formulations of the present invention in all aspects are preferably in ready-to-administer form, and are preferably stable in that form at room temperature and/or at 4° C. for at least one month, preferably at least 3 months, more preferably at least 6 months. By stable is meant that the lipid matrix part and any active agent present should be stable to oxidation under the specified conditions, such that at least 80% of the initial level of active bioactive agent content remains in its active form following storage for the specified period. Preferably, this will be at least 90% and most preferably at least 95% of the bioactive agent present before storage.

The invention will now be further illustrated by reference to the following non-limiting Examples, and the attached Figures, in which:

FIG. 1 Shows the effect of MTG concentration on the protection of buprenorphine (BUP) in the lipid formulation of the invention towards oxidation degradation during stress tests with hydrogen peroxide.

FIG. 2 Shows the recovery of BUP (HPLC) after 1 month at 70° C. (accelerated stability testing) as a function of MTG concentration in the formulation of the invention.

FIG. 3 Shows the assayed glucagon (GLU) content after storage at 25° C./60% RH for 7 days, plotted as the % of initial (time zero) GLU content, with different antioxidants included in the formulations.

FIG. 4 Shows the amount of detected degradation products (% Total Area) in GLU formulations after storage at 25° C./60% RH for 7 days, with different antioxidants included in the formulations.

EXAMPLES

Abbreviations used in examples:

| Name | Abbreviation | Supplier |
|---|---|---|
| Phosphatidylcholine, soy | SPC | Lipoid, Germany |
| Glycerol dioleate | GDO | Danisco, Denmark |
| Ethanol (99.5%) | EtOH | Kemetyl, Sweden |
| Mono-thioglycerol | MTG | Fluka, Sweden |
| N-acetyl cysteine | N—AcCys | Sigma-Aldrich, Sweden |
| α-tocopherol | TOC | DSM, Switzerland |
| Propyl gallate | PGall | Sigma-Aldrich, Sweden |
| Butyl hydroxytoluene | BHT | Fluka, Sweden |

Example 1 Effects of Different Antioxidants in Lipid Formulations of Buprenorphine (BUP)

Lipid formulations of BUP also containing antioxidant were prepared in the following way: First, a liquid lipid stock solution of SPC/GDO/EtOH/antioxidant (or a reference stock solution without antioxidant) in the required proportions were prepared by weighing of all components into glass vials followed by mixing by end-over-end rotation for about 8 h or until completely homogeneous liquids were obtained. Thereafter, BUP (powder) was added to achieve a nominal concentration of 7.9 wt % in all cases. The final nominal compositions of the respective formulations are given in Table 1. The antioxidants were added in an amount corresponding to common previous use in pharmaceutical products.

TABLE 1

Nominal compositions (wt %) of formulations studied

| Formulation | BUP | SPC | GDO | EtOH | MTG | PGall | TOC | BHT |
|---|---|---|---|---|---|---|---|---|
| A | 7.9 | 41.1 | 41.1 | 10.0 | — | — | — | — |
| B | 7.9 | 40.6 | 40.6 | 9.9 | 1.1 | — | — | — |
| C | 7.9 | 41.0 | 41.0 | 10.0 | — | 0.03 | — | — |
| D | 7.9 | 40.9 | 40.9 | 10.0 | — | — | 0.3 | — |
| E | 7.9 | 41.0 | 41.0 | 10.0 | — | — | — | 0.13 |

The following stress test was performed to evaluate the effect of the four different antioxidants (Table 1): Oxidative degradation was induced by adding 20 μL, $H_2O_2$ (30%)/mL formulation followed by equilibration of the formulations for 48 hours at RT (dark). Analysis of BUP and any oxidation degradation product (DP) in the formulations was performed by HPLC (reversed phase column) with UV detection at 288 nm. The relative retention time (RR) of BUP was set to 1 and the main oxidation DP had an RR of 1.053.

As shown in Table 2, all of the antioxidants had some effect compared with the reference formulation, however; MTG was clearly superior in protecting BUP from oxidation degradation in the lipid formulation.

TABLE 2

Effect of different antioxidants on BUP oxidation in stressed formulations ($H_2O_2$ treated formulations)

| Formulation | Antioxidant | Relative area % of main oxidation DP (RR = 1.053) |
|---|---|---|
| A | None (reference formulation) | 1.36 |
| B | MTG | 0.12 |
| C | PGall | 0.70 |
| D | TOC | 0.72 |
| E | BHT | 0.74 |

Example 2 Effect of Different MTG Concentrations

The protective effect of different MTG concentrations was assessed by performing a stress test according to Example 1. Briefly, to a lipid formulation of BUP with the nominal composition BUP/SPC/GDO/EtOH=7.9/41.1/41.1/10.0 wt % was added MTG at concentrations between 0-1.0 wt %. To the resulting formulations was added 20 μL $H_2O_2$ (30%)/mL formulation followed by equilibration for 48 hours at RT (dark). The formulations were thereafter analysed by HPLC as described in Example 1 and the relative area % of the main oxidation degradation product (DP) peak (relative retention RR=1.053) was determined. As shown in FIG. 1, already low concentrations of MTG had a significant protective effect.

Example 3 Effect of Different MTG Concentrations on BUP Stability During Accelerated Stability Studies Lipid formulations of BUP (nominal concentration 7.9 wt %) comprising different concentrations of MTG (0-1.0 wt %) were prepared as described in Examples 1 and 2. The formulations were filled in glass vials, the headspace flushed with nitrogen and the vials were capped with Teflon-coated rubber stoppers and tear-off aluminium caps. The vials were thereafter transferred to a heating cabinet held at 70° C. and stored for 1 month before HPLC analysis as described in Examples 1 and 2. As shown in FIG. 2, the addition of low concentrations of MTG increased the recovery of BUP from the stored samples.

Example 4 Lipid Formulation Comprising N-Acetyl Cysteine (N-AcCys)

A liquid lipid formulation comprising SPC/GDO/EtOH (42.5/42.5/15 wt %) was prepared by weighing all components in a glass vial followed by end-over-end mixing for 4 hours at RT. To the transparent and homogenous lipid formulation was added N-AcCys at a concentration of 0.25 wt % followed by further mixing for 12 hours. The resulting formulation was transparent and homogenous.

Example 5 Antioxidant Tests

To prevent breakdown of glucagon resulting from oxidation of the methionine residue (giving Met(O)27glucagon), an antioxidant may be included in the compositions of the present invention. To establish the most suitable antioxidant, various common and less common antioxidants were tested in the peptide/lipid system of the present invention.

The nominal composition of the samples used for the exploratory stability study is given in Table 3. Note that the antioxidant content in the respective formulations, except for the reference formulations (#229 and #234), was 0.3 wt % for tocopherol (α-TOC), acsorbyl palmitate (AscPalm) and mono-thioglycerol (MTG) and 0.1 wt % for butyl hydroxytoluene (BHT). Samples containing MTG were #233 and 235.

TABLE 3

Sample composition of formulations used for the exploratory stability study

| Formulation Number | Composition (wt %) (antioxidant additive in bold) |
|---|---|
| 229 | GLU/SPC/GDO/P80/EtOH/m-Cres/PG/BzCOOH = 0.3/31.2/31.2/3.9/11.8/0.5/20.1/1.0 |
| 230 | GLU/SPC/GDO/P80/EtOH/m-Cres/PG/BzCOOH/α-TOC = 0.3/31.1/31.1/3.9/11.7/0.5/20.1/1.0/0.3 |
| 231 | GLU/SPC/GDO/P80/EtOH/m-Cres/PG/BzCOOH/ AscPalm = 0.3/31.1/31.1/3.9/11.7/0.5/20.1/1.0/0.3 |
| 232 | GLU/SPC/GDO/P80/EtOH/m-Cres/PG/BzCOOH/BHT = 0.3/31.15/31.15/3.85/11.75/0.5/20.1/1.0/0.1 |
| 233 | GLU/SPC/GDO/P80/EtOH/m-Cres/PG/BzCOOH/MTG = 0.3/31.1/31.1/3.9/11.7/0.5/20.1/1.0/0.3 |
| 234 | GLU/DOPC/GDO/P80/EtOH/m-Cres/PG/BzCOOH = 0.3/31.2/31.2/3.9/11.8/0.5/20.1/1.0 |
| 235 | GLU/DOPC/GDO/P80/EtOH/m-Cres/PG/BzCOOH/MTG = 0.3/31.1/31.1/3.9/11.7/0.5/20.1/1.0/0.3 |

GLU = glucagon;
SPC = Soy phosphatidylcholine;
GDO = Glyceroldioleate;
P80 = Polysorbate 80;
EtOH = Ethanol;
PG = Propylene glycol;
m-Cres = meta-Cresol;
BzCOOH = Benzoic acid The stability data using a number of different antioxidants above have shown that MTG is more efficient than other lipid soluble antioxidants in suppressing the oxidative degradation of glucagon. This effect is outlined in the above Table and discussed by reference to the Figures below.

In FIG. 3, the assayed GLU content after storage at 25° C./60% RH for 7 days is plotted as the % of initial (time zero) GLU content. It can be seen that MTG gave best oxidation protection, with only this and BHT being better than the control (antioxidant-free) composition. α-tocopherol and AscPalm were degrading of glucagon in these tests.

FIG. 4 displays the amount of detected degradation products (% Total Area) with a relative retention RR<1 and RR>1, respectively, as compared with the peak corresponding to GLU. Because the assay is based on a normal phase (NP) HPLC column, degradation products with RR<1 are more hydrophobic compared with GLU whereas more hydrophilic degradation products give RR>1.

The major part of the detected degradation products with RR>1 is constituted by oxidized glucagon (Met(O)27glucagon). It is clearly seen that MTG is most efficient in preventing the formation of Met(O)27glucagon.

The invention claimed is:
1. A depot formulation comprising:
  i) a lipid matrix;
  ii) at least one thiolated antioxidant;
  iii) optionally at least one bioactive agent; and
  iv) optionally at least one chelating agent;
  wherein said lipid matrix comprises:
    a) at least one diacyl glycerol and/or tocopherol;
    b) at least one phospholipid;
    c) at least one oxygenated organic solvent; and
    d) optionally at least one fragmentation agent;
  wherein the formulation may comprise up to 20 wt. % water provided that at least 3% wt. % of c) is also present; and
  wherein the formulation generates at least one non-lamellar phase upon exposure to an aqueous fluid.
2. A formulation as claimed in claim 1, wherein the thiolated antioxidant is a thiolated sugar, thiolated amino acid, a thiolated amino ester, or a thiolated polyol.
3. A formulation as claimed in claim 2, wherein said thiolated antioxidant is selected from the group consisting of mono-thioglycerol, cysteine and N-acetyl cysteine.
4. A formulation as claimed in claim 1, wherein said bioactive agent is present and is an agent susceptible to oxidative degradation.
5. A formulation as claimed in claim 4, wherein said bioactive agent is at least one active pharmaceutical ingredient.
6. A formulation as claimed in claim 1 additionally comprising a chelating agent.
7. A formulation as claimed in claim 1 additionally comprising a lipid soluble acid.
8. A method for reducing oxidative degradation in a depot formulation comprising a lipid matrix and at least one bioactive agent, said method comprising adding at least one thiolated antioxidant and optionally at least one chelating agent,
  wherein said lipid matrix comprises:
    a) at least one diacyl glycerol and/or tocopherol;
    b) at least one phospholipid;
    c) at least one oxygenated organic solvent; and
    d) optionally at least one fragmentation agents;
  wherein the formulation may comprise up to 20 wt. % water provided that at least 3% wt. % of c) is also present; and
  wherein the formulation generates at least one non-lamellar phase upon exposure to an aqueous fluid.

9. A method as in claim 8, wherein the chelating agent is added and is EDTA.

10. A method as in claim 8, further comprising adding at least one lipid soluble acid.

11. A formulation as in claim 1, wherein the at least one thiolated antioxidant is present in an amount of 0.01 to 2.0% by weight.

12. A method as in claim 8, wherein the at least one thiolated antioxidant is present in an amount of 0.01 to 2.0% by weight.

13. A formulation as claimed in claim 1, wherein said bioactive agent is leuprorelin.

\* \* \* \* \*